United States Patent [19]

Levine et al.

[11] 4,036,693

[45] July 19, 1977

[54] TREATMENT OF CELL CULTURE MICROCARRIES

[75] Inventors: David W. Levine, Somerville; William G. Thilly, Cambridge; Daniel I. C. Wang, Belmont, all of Mass.

[73] Assignee: Massachusetts Institute of Technology, Cambridge, Mass.

[21] Appl. No.: 654,134

[22] Filed: Feb. 2, 1976

[51] Int. Cl.² .............................................. C12B 3/00
[52] U.S. Cl. .................................................... 195/1.8
[58] Field of Search ......................................... 195/1.8

[56] References Cited

U.S. PATENT DOCUMENTS 3,850,748  11/1974  Cook et al. .................... 195/1.8
3,910,819  10/1975  Rembaum et al. .................... 195/1.8

*Primary Examiner*—Sam Rosen
*Attorney, Agent, or Firm*—Arthur A. Smith, Jr.; Robert Shaw; David E. Brook

[57] ABSTRACT

A method of treating certain cell culture microcarriers to improve their performance is disclosed. In this method, positively charged microcarriers, such as those produced by reacting polydextran beads with diethylaminoethyl, are treated by contacting them with macromolecular polyanions, such as carboxymethylcellulose, prior and/or during use in cultures. Such treatment overcomes deleterious effects previously observed in attempts to use these microcarriers in cell culture systems.

14 Claims, 6 Drawing Figures

TREATMENT OF CELL CULTURE MICROCARRIES

The Government has rights in this invention pursuant to Grant No. Y-10754 and IPA-0010 awarded by the National Science Foundation.

BACKGROUND OF THE INVENTION

1. Field of the Invention

This invention is in the field of biology and more particularly in the field of cell biology.

2. Description of the Prior Art

The ability to grow mammalian cells is important at both the laboratory and industrial levels. At the laboratory level, the limiting factor for cellular or viral research at the sub-cellular level is often the amount of raw material available to be studied. At the industrial level, there is much effort being devoted to the development of pharmaceuticals based on mammalian cell products. These are primarily vaccines for human viruses, but also include human growth hormone and other body hormones for medical applications.

Some mammalian cell types have been adapted for growth in suspension cultures. Examples of such cell types include HeLa (human), BHK (baby hamster kidney) and L mouse cells. Such cells, in general, have non-normal genetic complements, i.e., too many or too few chromosomes or abnormal chromosomes. Often, these cells will produce a tumor upon injection into an animal of the appropriate species.

Other mammalian cell types have not been adapted for growth in suspension culture to date, and will grow only if they can become attached to an appropriate surface. Such cell types are generally termed "anchorage-dependent" and include 3T3 mouse fibroblasts, mouse bones marrow epithelial cells; Murine luekemia virus producing strains of mouse fibroblasts, primary and secondary chick fibroblasts; WI-38 human fibroblast cells; and, normal human embryo lung fibroblast cells (HEL299, ATCC CCL137 ). Some anchorage-dependent cells have been grown which are tumor causing but others were grown and found to be non-tumor causing. Also, some anchorage-dependent cells, such as WI-38 and HEL299, can be grown which are genetically normal.

Whereas considerable progress has been made in large scale mammalian cell propagation using cell lines capable of growth in suspension culture, progress has been very limited for large scale propagation of anchorage-dependent mammalian cells. Previous operational techniques employed for large scale propagation of anchorage-dependent cells were based on linear expansion. Cell culture plants utilized a large number of low yield batch reactors, in the forms of dishes, prescription bottles, roller tubes and roller bottles. Each of these was a discrete unit or isolated batch reactor requiring individual environmental controls. These controls, however, were of the most primative type due to economic considerations. Variation in nutrients was corrected by a medium change, an operation requiring two steps, i.e., medium removal and medium addition. Since it was not uncommon for a moderately sized facility to operate hundreds of these batch reactors at a time, even a single change of medium required hundreds of operations, all of which had to be performed accurately, and under exacting sterile conditions. Any multiple step operation, such as cell transfer or harvest, compounded the problem accordingly. Thus, costs of equipment, space and manpower were great for this type of facility.

There are alternative methods to linear scale-up from small batch cultures which have been proposed. Among such alternatives which have been reported in the literature are plastic bags, stacked plates, spiral films, glass bead propagators, artificial capillaries, and microcarriers. Among these, microcarrier systems offer certain outstanding and unique advantages. For example, great increases in the attainable ratio of growth surface to vessel volume (S/V) can be obtained using microcarriers over both traditional and newly developed alternative techniques. The increase in S/V attainable allows the construction of a single-unit homogeneous or quasi-homogeneous batch or semi-batch propagator for high volumetric productivity. Thus, a single stirred tank vessel with simple feedback control for pH and pO2 presents a homogeneous environment for a large number of cells thereby eliminating the necessity for expensive and space consuming, controlled environment incubators. Also, the total number of operations required per unit of cells produced is drastically reduced. In summary, microcarriers seem to offer economies of capital, space and manpower in the production of anchorage-dependent cells, relative to current production methods.

Microcarriers also offer the advantage of environmental continuity since the cells are grown in one controlled environment. Thus, microcarriers provide the potential for growing anchorage-dependent mammalian cells under one set of environmental conditions which can be regulated to provide constant, optimal cell growth.

One of the more promising microcarrier systems to date has been reported by van Wezel and involves the use of polydextran beads reacted with diethylaminoethyl (DEAE) in a stirred tank. A. L. van Wezel, "Growth of Cell Strains and Primary Cells on Microcarriers in Homogeneous Culture", *Nature* 216:64 (1967 ); D. van Hemert, D. G. Kilburn and A. L. van Wezel, "Homogeneous Cultivation of Animal Cells for the Production of Virus and Virus Products", *Biotechnol. Bioeng.* 11:875 (1969 ); and A. L. van Wezel, "Microcarrier Cultures of Animal Cells", *Tissue Culture, Methods and Applications,* P. F. Kruse and M. K. Patterson, eds., Academic Press, New York, p. 372 (1973 ). These beads are commercially produced by Pharmacia Fine Chemicals, Inc., Piscataway, New Jersey, under the tradename DEAE-Sephadex A50, an ion exchange system. Chemically, these beads are formed from a crosslinked dextran matrix having diethylaminoethyl groups covalently bound to the dextran chains. As commercially available, DEAE-Sephadex A50 beads have a particle size of 40–120μ and a charge capacity of 3.5 ± 0.5 meq/gm dry material. Other anion exchange resins, such as DEAE-Sephadex A25, QAE-Sephadex A50 and QAE-Sephadex A25 were also shown by van Wezel to support cell growth.

The system proposed by van Wezel combines multiple surfaces with moveable surfaces and has the potential for innovative cellular manipulations and offers advantages in scale-up and environmental controls. Despite this potential, however, these suggested techniques have not been significantly exploited which is probably because of difficulties encountered in cell production due to deleterious effects which the beads seem to exhibit and which prevent good cell growth. For example, van Wezel's published data indicate that, even with bead washings and pretreatments, up to 75% of the inoculum has been lost using the DEAE-treated polydextran beads.

SUMMARY OF THE INVENTION

This invention relates to the treatment of positively charged cell culture microcarriers, such as DEAE-treated polydextran beads, to overcome the previously noted deleterious effects on cell growth. Beads are contacted with macromolecular polyanions, such as carboxymethylcellulose, prior and/or during cell growth. In the growth of certain anchorage-dependent mammalian cells, and particularly in cultures with relatively high carrier concentrations, macromolecular polyanion can also be supplied with medium replenishment.

The treatment techniques described herein allow the use of microcarrier systems in the large scale propagation of anchorage-dependent cells. Thus, the enormous potential offered by microcarrier systems can be finally realized.

DESCRIPTION OF PREFERRED EMBODIMENTS

Figure 1:
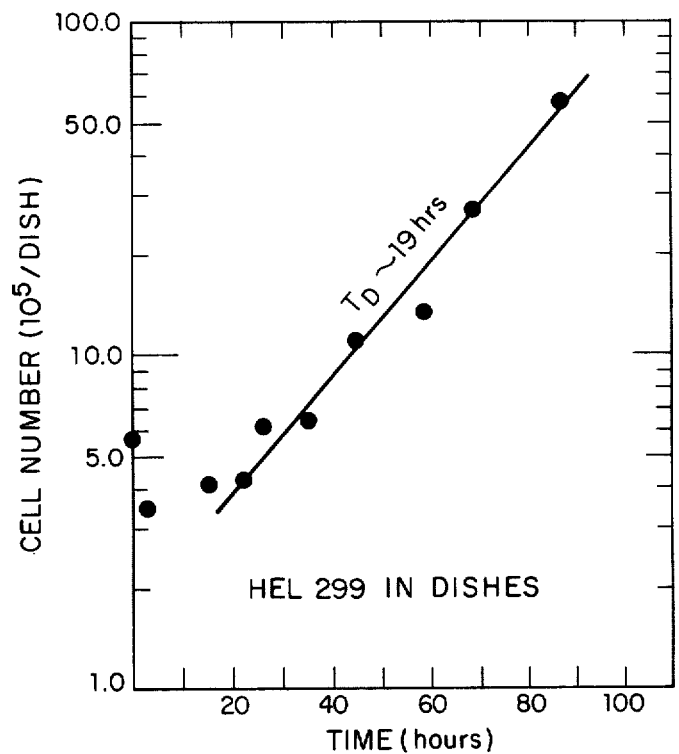
FIG. 1 illustrates graphically the growth characteristics of normal human embryo lung fibroblast cells (HEL299) on dishes.

As discussed above, microcarriers provide outstanding support surfaces for growth of anchorage-dependent mammalian cells. Microcarriers are small discrete particles suitable for cell attachment and growth and are generally in the form of porous beads which have outer and inner surfaces. Usually, cells attach to and grow on the outer surfaces of such beads. Recently, it has been found that microcarriers having positive charges, at their surfaces function well in microcarrier cultures. Some examples of commercially available microcarriers having positive charges on their surfaces are those ion exchange resins sold under the tradenames DEAE-Sephadex A50, DEAE-Sephadex A25, Amberlite IR-45 and BioRad AG-21K. Those skilled in the art of growing anchorage-dependent mammalian cells will know others, or be able to ascertain them using no more than routine experimentation.

Microcarrier bead treatment is done by contacting the carriers with a macromolecular polyanion. A convenient way to accomplish the treatment is to suspend microcarriers in a solution of a macromolecular polyanion. A preferred method of achieving such contact is by suspending the beads in agitated culture medium containing a macromolecular polyanion prior to cell inoculation and until an equilibrium is reached. Alternatively, a macromolecular polyanion can be added to the culture medium containing untreated beads at any time prior to cell inoculation. Also, the beads could be pretreated with other solutions or suspensions of a macromolecular polyanion, the important consideration being that the bead surfaces are brought into contact with the polyanion, prior or simultaneously with cell inoculation, or even subsequent to cell inoculation as long as the polyanion contacts the microcarriers before significant deleterious effects occur.

While not wishing to be bound by the following theory, it is believed that the macromolecular polyanion is effective in improving cell growth because it competes with medium and cell produced nutrients for adsorptive sites on the microcarrier surfaces where cells do not attach. This may be particularly true with regard to internal surfaces of voids within the porous beads. Since most cells cannot penetrate into such bead voids, the adsorption of cell nutrients at those surfaces, in the absence of the macromolecular polyanion, depletes the nutrient supply available to the growing cells. Because the porous beads have relatively high amounts of internal surface area, there is a drastic reduction in the nutrients available to growing cells. By eliminating the adsorption of nutrients at these internal adsorptive sites, the macromolecular polyanions prevent such significant losses of nutrients to the growing cells and thereby overcome the deleterious effects of microcarrier systems which were previously encountered.

In some cases, where the molecular weight is sufficiently low, the macromolecular polyanion is believed to enter the bead pores and bind to the internal pore surfaces. In such cases, an adsorptive site for nutrients is thus eliminated. It is not essential, however, for the macromolecular polyanion to have a molecular weight low enough to allow it to enter the pores of microcarriers. It has also been found that good cell growth can be achieved with microcarriers treated with macromolecular polyanions having a molecular weight too large to allow them to penetrate into the beads. It is believed that the higher molecular weight polyanions form a thin coating on the outer bead surfaces which acts as a barrier to nutrients entering the pores. Cells are able to attach to the outer bead surfaces even with this outer coating, and such cells grow quite well. The crux of the treatment is, therefore, contacting the microcarriers with a macromolecular polyanion to prevent adsorptive sites where cells cannot attach from taking up appreciable amounts of cell nutrients.

In view of the above, it can be appreciated that molecular weight is an important parameter of suitable polyanions. The molecular weight must be large enough to provide sufficient charges upon the polyanion so that it will remain bound to bead surfaces once it becomes attached. On the other hand, it should not be so high as to interfere with its capability to reach the surfaces of the bead. Therefore, the macromolecular polyanion should have a molecular weight (Mw) of between about 600 and about 200,000, and preferably has a molecular weight of between about 10,000 and 100,000.

In addition to the proper molecular weight, the macromolecular polyanion must also be nontoxic to growing mammalian cells. In this context, the term "nontoxic" is used to include polyanions which do not kill growing cells, and further, which do not significantly interfere with normal cell metabolism.

Some specific macromolecular polyanions which are suitable include negatively charged polysaccharides and proteins. Some examples of suitable polysaccharides include cellulose, starch, dextran, xylan and solubilized gum arabic. The negative charges can be supplied by pendant negative groups including sulfate, phosphate, carboxyl and acetate. Carboxymethylcellulose is particularly preferred because of the outstanding results it produces, but those skilled in the art will recognize other suitable macromolecular polyanions following the teachings contained herein.

The concentration of macromolecular polyanion used will, of course, depend upon such factors as the specific macromolecular polyanion chosen, its molecular weight, the specific microcarrier, the concentration of microcarrier, and the specific cells grown. In general, it is desirable to coat all surfaces where cells cannot attach with at least a monomolecular layer of polyanion. On the other hand, too large an excess of polyanion is believed to be detrimental to cell growth.

With some mammalian cells, macromolecular polyanion can also be added to the cell culture on a continuous basis or quasicontinuous basis. Typically, this is done by adding macromolecular polyanion with cell replenishment.

The invention is further illustrated by the following examples.

EXAMPLE 1

GROWTH OF NORMAL HUMAN EMBRYO LUNG FIBROBLASTS (HEL299) IN DISHES

Human embryo lung cells (HEL299, ATCC CCL137) were used as passage 7 and 8. These were obtained frozen from the American Type Culture Collection at passage 4 and maintained in dishes for two passages (at 1:10) before being refrozen and stored under liquid nitrogen. Dulbecco-modification of Eagle's medium supplemented with 10% fetal calf serum was added.

HEL299 cells were harvested from a confluent 100 mm plate with 0.1% trypsin solution. After the cells were detached, the trypsin was quenched with fetal calf serum in the ratio of 1 ml serum per 5 ml trypsin solution. The resulting cell suspension was centrifuged at 1500 r.p.m. for 10 minutes, after which the trypsin/fetal calf serum supernatant was drawn off. Remaining cells were suspended in 100 ml of fresh medium. 10 ml of the new suspension was then added to a fresh 100 mm plastic tissue culture dish (Optilux 3002). Plates were periodically poured off and cells were stained with 0.1 M citrate: 0.1% Crystal Violet. This allowed the total number of cells per plate to be determined with a hemocytometer.

The growth characteristics of this culture are plotted in FIG. 1. As can be seen, approximately 60% of the inoculum attached to the surface as potentially growing cells. The overall culture doubling time was 18–20 hours.

EXAMPLE 2

GROWTH OF NORMAL HUMAN EMBRYO LUNG FIBROBLASTS (HEL299) IN MICROCARRIER CULTURE AT 1 MG/ML WITHOUT BEAD PRETREATMENT

Spinner cultures consisting of glass bottles having 100 ml working volume and approximately 150 ml of head space were used. These glass bottles were siliconized to prevent adhesion of both cells and microcarriers to the sides, and cultures were agitated by suspended magnetic spinners with the ratio of bottle diameter to spinner length being 1.4. Agitation speed was fixed at 80–90 r.p.m.

DEAE-Sephadex A50 beads, obtained from Pharmacia, were used. The dry beads were sieved to obtain a uniform bead size of $>90\mu$, $<105\mu$. Sieved beads were suspended in a phosphate buffered saline solution and autoclaved, and this sequence was then repeated five times. The beads were stored in phosphate buffered saline at room temperature and stock solutions of carrier beads of 10 mg/ml were prepared. Before use, the beads were settled and excess phosphate buffered saline was removed. Beads were then suspended in an appropriate amount of medium. At 1 mg/ml, the spinners had a culture area of 2.3 cm$^2$/ml of culture volume.

The pH in the spinner culture was controlled by a 5% $CO_2$: 95% air overlay and a bicarbonate buffering system.

Inoculation was done as follows. An appropriate aliquot of stock solution containing 1 mg/ml carriers was allowed to settle, excess saline solution was drawn off, and Dulbecco-modification of Eagle's medium supplemented with 10% fetal calf serum was added to suspend the beads. The suspension was then transferred under sterile conditions to the growth vessel to which cells were added directly. After the carriers had been agitated for 12 hours, depleted medium was removed and fresh medium supplement was added.

The HEL299 cells were obtained and prepared in the same manner as in Example 1. Inoculation was generally done with exponetial phase, or late exponential phase cells, grown on dishes. Trypsin used in harvesting was neutralized by fetal calf serum, and the cells removed from the solution by centrifugation. Cells were then suspended in growth medium for inoculation.

Figure 2:
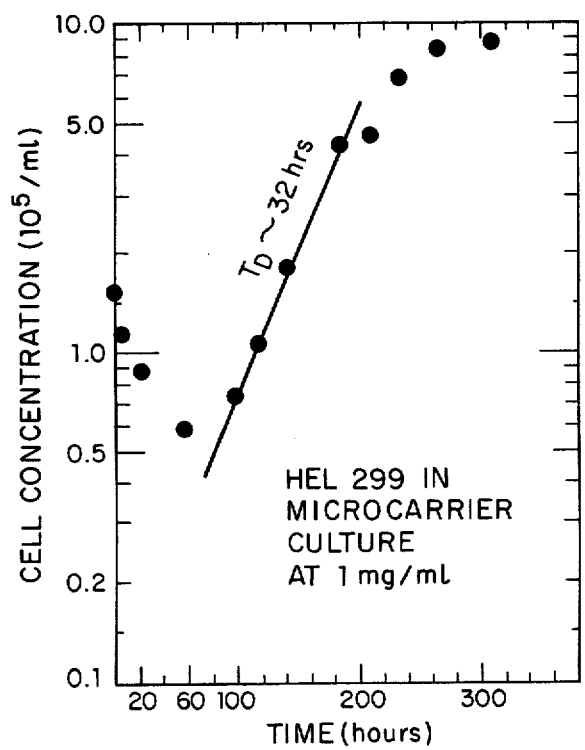
FIGS. 2-3 illustrate graphically the growth characteristics of normal human embryo lung fibroblast cells (HEL299) in microcarrier culture at 1 mg/ml and 4 mg/ml, respectively, without bead treatment as described herein; and, FIGS. 4-6 illustrate graphically the growth characteristics of normal human embryo fibroblast cells (HEL299) on treated microcarrier beads at bead densities of 1, 2 and 4 mg/ml, respectively, at different concentrations of carboxymethylcellulose.

The growth characteristics of this culture are plotted in FIG. 2 wherein it can be seen that nearly 70% of the inoculum disappeared from the culture within 24 hours and was therefore not available for growth. The culture doubling time was 30 hours.

EXAMPLE 3

GROWTH OF NORMAL HUMAN EMBRYO LUNG FIBROBLASTS (HEL299) IN MICROCARRIER CULTURE AT 4 MG/ML WITHOUT BEAD PRETREATMENT

Figure 3:
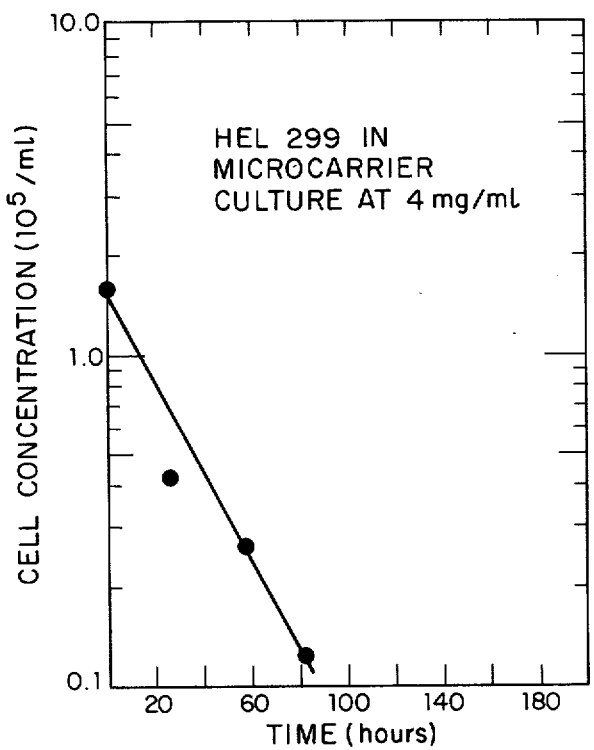
Figure 4:
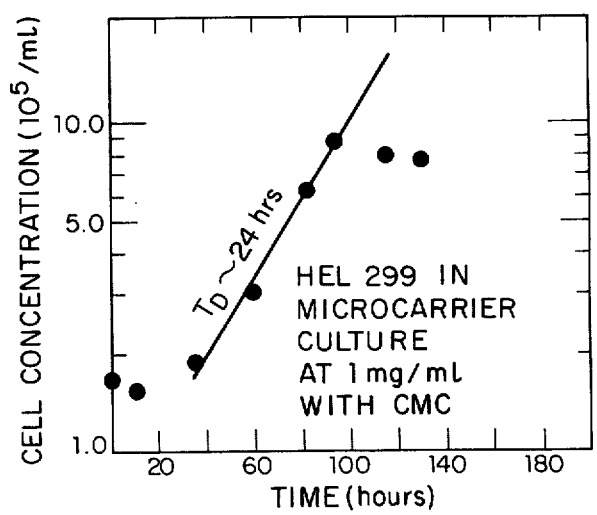

The procedure, apparatus and materials of Example 2 were used except that the microcarrier bead concentration was 4 mg/ml. The growth characteristics are plotted in FIG. 3 wherein it can be seen that the entire cell inoculum was lost.

EXAMPLE 4

GROWTH OF NORMAL HUMAN EMBRYO LUNG FIBROBLASTS (HEL299) IN MICROCARRIER CULTURE AT 1 MG/ML WITH CARBOXYMETHYLCELLULOSE ADDITION

The procedure, apparatus and materials of Example 2 were used except that 0.01 grams of carboxymethylcellulose (Hercules CMC Gum 7H4F), molecular weight approximately 150,000–200,000, was added per liter of growth medium. Medium replenishment was carried out about once a day by stopping agitation to allow the beads to settle followed by removal of 25 ml of medium and replacement with 25 ml of fresh medium containing 0.01 g carboxymethylcellulose per liter. As can be seen, very little of the initial inoculum was lost and good growth rates were obtained.

EXAMPLE 5

GROWTH OF NORMAL HUMAN EMBRYO LUNG FIBROBLASTS (HEL299) IN MICROCARRIER CULTURE AT 2 MG/ML WITH CARBOXYMETHYLCELLULOSE ADDITION

Figure 5:
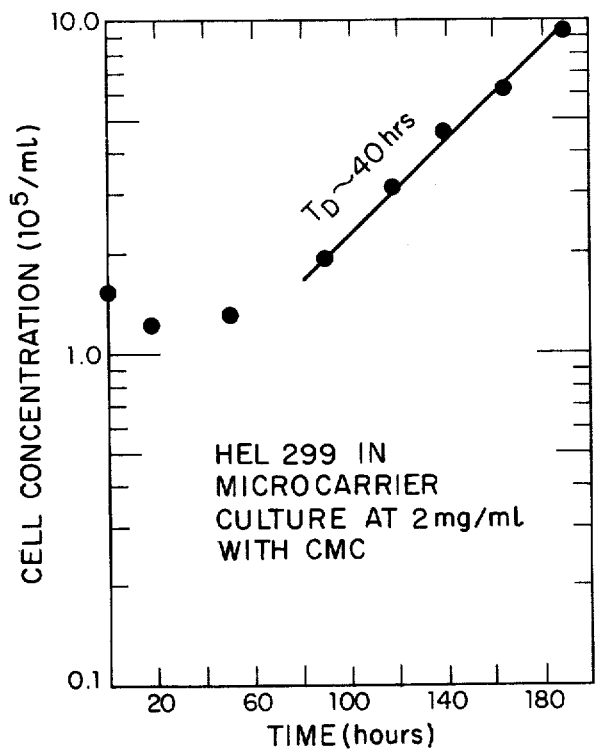

The procedure, apparatus and materials of Example 4 were used except as follows. The carrier concentration was set at 2 mg/ml and the initial and replenishment growth medium contained 0.05 gm carboxymethylcellulose (Hercules CMC Gum 7L2, M. W. ~ 45,000) per liter. The growth characteristics are plotted in FIG. 5. It can be seen that little of the cell inoculum is lost and growth is exponential up to $10^6$ cells/ml.

EXAMPLE 6

GROWTH OF NORMAL HUMAN EMBRYO LUNG FIBROBLASTS (HEL299) IN MICROCARRIER CULTURE AT 4 MG/ML WITH BEAD PRETREATMENT WITH CARBOXYMETHYLCELLULOSE

Figure 6:
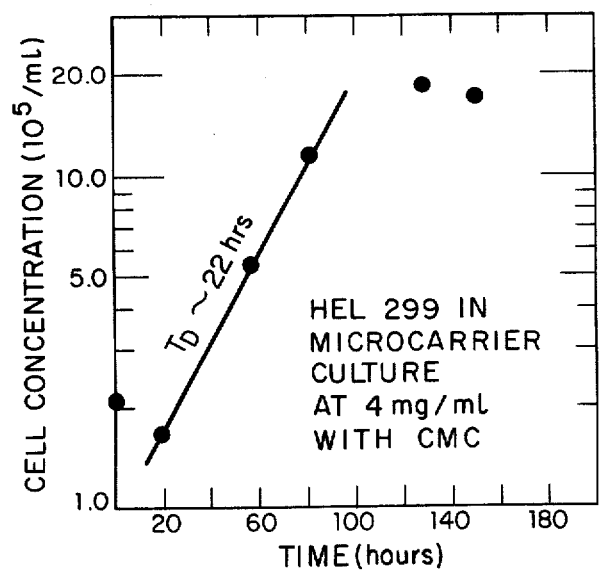

The procedure, apparatus and materials were generally the same as in Example 4 with some changes as follows. The microcarrier concentration used was 4 mg/ml and the beads were kept in contact with growth medium containing 0.04 gm carboxymethylcellulose (Hercules CMC Gum 7H4F) per liter of medium for 12 hours at 37° C before cell inoculation. Immediately prior to inoculation, the growth medium was removed and replaced with fresh growth medium containing 0.01 gm carboxymethylcellulose per liter — this served as the final growth medium. Replenishment medium also contained 0.01 g carboxymethylcellulose per liter. The growth characteristics are plotted in FIG. 6 wherein it can be seen that little decrease in cell inoculum occurred and a strong exponential phase growth up to the final density of $2 \times 10^6$ cell/ml occurred. This final density is comparable to densities obtained in suspension cultures with such cells. Specifically, less than 2% of the total cell population was not associated with the carriers, cell yield on a per medium basis was comparable to that obtained with dishes, and cells could easily be recovered from the carriers by standard trypsinization.

Those skilled in the art will know, or be able to ascertain by no more than routine experimentation, many equivalents to the specific embodiments expressly described herein. For example, although the description herein has been mainly in terms of anchorage-dependent mammalian cells, the invention applies as well to non-mammalian cells, such as avian or amphibian cells, as long as they are anchorage-dependent. Such equivalents are within the scope of this invention and are intended to be covered by the appended claims.

What is claimed is:

1. In the method of growing anchorage-dependent cells in a suspension of positively charged microcarriers in culture medium:
   the improvement comprising treating said microcarriers by contacting them with a nontoxic macromolecular polyanion.

2. An improvement of claim 1 wherein said macromolecular polyanion is a cellulose.

3. An improvement of claim 2 wherein said macromolecular polyanion has a molecular weight of between about 600 and about 200,000.

4. an improvement of claim 3 wherein said microcarriers are positively-charged polydextran microcarriers.

5. An improvement of claim 1 wherein said macromolecular polyanion is carboxymethylcellulose.

6. An improvement of claim 4 wherein said macromolecular polyanion is carboxymethylcellulose.

7. An improvement of claim 6 wherein said microcarriers are contacted with said carboxymethylcellulose prior to cell inoculation.

8. An improvement of claim 7 wherein medium replenishments containing carboxymethylcellulose are added to said culture medium.

9. A method of treating positively-charged cell culture microcarriers to enhance their cell growing characteristics comprising contacting said microcarriers with a nontoxic macromolecular polyanion.

10. A method of claim 9 wherein said macromolecular polyanion is a negatively-charged polysaccharide or protein.

11. A method of claim 9 wherein said macromolecular polyanion is carboxymethylcellulose.

12. A method of claim 11 wherein said microcarriers are positively-charged polydextran microcarriers.

13. Cell culture microcarriers produced by the method of claim 9.

14. Cell culture microcarriers produced by the method of claim 12.